United States Patent [19]

Langerbeins

[11] Patent Number: 5,070,061
[45] Date of Patent: Dec. 3, 1991

[54] HETEROPOLYMOLYBDATE CATALYSTS AND METHOD FOR OXYDEHYDROGENATION

[75] Inventor: Klaus Langerbeins, Mannheim, Fed. Rep. of Germany

[73] Assignee: Röhm GmbH, Darmstadt, Fed. Rep. of Germany

[21] Appl. No.: 625,649

[22] Filed: Dec. 7, 1990

Related U.S. Application Data

[63] Continuation-in-part of Ser. No. 390,487, Aug. 1, 1989, abandoned, which is a continuation of Ser. No. 78,223, Jul. 27, 1987, abandoned.

[30] Foreign Application Priority Data

Aug. 2, 1986 [DE] Fed. Rep. of Germany ....... 3626256

[51] Int. Cl.$^5$ ............................................. B01J 27/186
[52] U.S. Cl. ..................................... 502/211; 502/209; 502/210; 502/212; 502/213; 502/214; 562/599
[58] Field of Search ............... 502/209, 210, 211, 212, 502/213, 214; 562/599

[56] References Cited

U.S. PATENT DOCUMENTS

| | | | |
|---|---|---|---|
| 4,061,673 | 12/1977 | Onoda et al. ........................ | 562/599 |
| 4,146,574 | 3/1979 | Onoda et al. ........................ | 423/299 |
| 4,273,676 | 6/1981 | Matsumoto et al. ................ | 252/435 |
| 4,522,934 | 6/1985 | Shum et al. ......................... | 502/209 |
| 4,568,801 | 1/1986 | Shimizu et al. ..................... | 502/209 |
| 4,720,575 | 1/1988 | Gruber ................................ | 560/214 |

FOREIGN PATENT DOCUMENTS

| | | |
|---|---|---|
| 1194014 | 9/1985 | Canada . |
| 31729 | 7/1981 | European Pat. Off. ........... 502/209 |
| 0079491 | 5/1983 | European Pat. Off. . |
| 0113084 | 7/1984 | European Pat. Off. . |
| 2722375 | 12/1977 | Fed. Rep. of Germany . |
| 3019731 | 12/1981 | Fed. Rep. of Germany . |
| 3248600 | 7/1984 | Fed. Rep. of Germany . |
| 2407022 | 5/1979 | France . |
| 1523849 | 9/1978 | United Kingdom . |

OTHER PUBLICATIONS

Tsigdinos, Ind. Eng. Chem., Prod. Res. Develop. 13, 267–274 (1974).
Otake et al., Studies Surface Science and Catalysis 7, 780–791 (1981).

Primary Examiner—Willliam R. Dixon, Jr.
Assistant Examiner—Anthony J. Green

[57] ABSTRACT

Catalysts containing molybdenum, vanadium, phosphorus, and oxygen, optionally together with one or more metal ions, as their active constituents, are preferably disposed on an inert carrier for the oxidative dehydrogenation of isobutyric acid or its lower esters to methacrylic acid or its lower esters.

9 Claims, No Drawings

HETEROPOLYMOLYBDATE CATALYSTS AND METHOD FOR OXYDEHYDROGENATION

This application is a continuation-in-part of application Ser. No. 07/390,487, filed Aug. 1, 1989 and now abandoned, which in turn is a continuation of application Ser. No. 07/078,223 filed July 27, 1987 and now abandoned.

The present invention relates to mixtures of heteropolyacid compounds, particularly to mixtures of phosphomolybdic acid and vanadium-containing derivatives of phosphomolybdic acid and their salts, and to methods for the oxydehydrogenation of isobutyric acid or its esters to methacrylic acid or its esters using such mixtures as catalysts.

THE PRIOR ART

12-Molybdophosphoric acid, $H_3PMo_{12}O_{40} \cdot xH_2O$, also known as phosphomolybdic acid, can be prepared, for example, by reacting molybdenum trioxide in heated dilute phosphoric acid, in other words, hydrothermally. [Tsigdinos, Ind. Eng. Chem., Prod. Res. Develop. 13, 267 (1974)].

This phosphomolybdic acid can be used as a heteropolyacid catalyst in the oxydehydrogenation of isobutyric acid to methacrylic acid, which proceeds by heterogeneous catalysis. However, the selectivity of this catalytically active substance for methacrylic acid has an unsatisfactory value of only 40 percent. [Otake et al., Studies Surface Science and Catalysis 7, 780–791 (1981)]. In contrast thereto, a heteropolyacid catalyst with $H_5PMo_{10}V_2O_{40}$, a vanadium derivative of phosphomolybdic acid with a selectivity for methacrylic acid of 73 percent, is considerably more selective and has practically the same activity, according to the same authors. Vanadium derivatives of phosphomolybdic acid such as $H_5PMo_{10}V_2O_{40}$ or $H_4PMo_{11}VO_{40}$ can be prepared inter alia hydrothermally, as described in German Patent Publication 27 22 375, (U.S. Pat. No. 4,146,574) by heating stoichiometric amounts of $MoO_3$ and $V_2O_5$ in water containing $H_3PO_4$.

As the applicant's own tests have shown, oxydehydrogenation catalysts containing the heteropolyacid $H_4PMo_{11}VO_{40}$ as the catalytically active substance, which catalysts have a selectivity for methacrylic acid of about 60 percent, are significantly less selective than oxydehydrogenation catalysts containing $H_5PMo_{10}V_2O_{40}$. While $H_3PMo_{12}O_{40}$ is quite unsuitable for use as a catalyst in a commercial process because of its low selectivity, $H_4PMo_{11}VO_{40}$, used as a catalyst, and especially the relatively selective $H_5PMo_{10}V_2O_{40}$ or $H_6PMo_9V_3O_{40}$ catalysts, lack the long term characteristics required from the technical and economic points of view.

Catalysts prepared from metallic salts of heteropolyacids, for example $H_{7.6}Cu_{0.2}PMo_{10}VO_{39}$ or its anhydride, $Cu_{0.2}PMo_{10}VO_{35.2}$, which are known from German Patent Publication 32 48 600 for the oxydehydrogenation of isobutyric acid or its esters and which are prepared hydrothermally in the presence of a copper compound and have high selectivities for methacrylic acid of up to about 83 percent in the oxydehydrogenation of isobutyric acid, also exhibit an unsatisfactory long term behavior.

THE OBJECT AND THE INVENTION

Thus, there has been a need for developing heteropolyacid derivatives comprising phosphomolybdic acid which, when used as catalysts for the oxydehydrogenation of isobutyric acid or its esters to methacrylic acid or its esters, exhibit not only good activity and selectivity but also exhibit long term behavior which is technically satisfactory.

According to the present invention, it has been found that compositions of various heteropolyacids comprising phosphomolybdic acid which have an atomic ratio of Mo:V wherein Mo is greater than 9 and less than 12 and V is 0.1 or greater but less than 3 surprisingly have long term stability when used as oxydehydrogenation catalysts. The heteropolyacid derivatives used in accordance with the invention are compositions of various heteropolyacids comprising phosphomolybdic acid, such as $H_3PMo_{12}O_{40}$ and/or $H_{3+x}PMo_{12-x}V_xO_{40}$, wherein x is 1, 2, or 3, or salt derivatives thereof, and they may be mixtures of the various starting heteropolyacids or their salts as well as mixtures containing further compounds formed during preparation.

The invention thus relates to catalysts containing molybdenum, vanadium, phosphorus, and oxygen, and optionally one or more metal ions, as the active constituents, which catalysts are preferably disposed on an inert carrier and are useful for the oxidative dehydrogenation of isobutyric acid or its lower esters to form methacrylic acid or its esters. The catalytically active constituent of the catalyst is, or is formed from, a heteropolymolybdate mixture of phosphomolybdic acid, $H_3PMo_{12}O_{40}$, or its salts and/or its vanadium derivatives, $H_{3+x}PMo_{12-x}V_xO_{40}$, wherein x is 1, 2, or 3, and/or their salts.

The catalyst corresponds to a heteropolymolybdate mixture of the formula $H_aM_bP_cMo_dV_eO_f$, wherein M is a cation of one or more of the metallic elements Li, Na, K, Rb, Cs, Be, Mg, Ca, Sr, Ba, Zn, Cd, Al, Ce, Ti, Zr, Sn, Sb, Pb, Bi, Cr, Mn, Fe, Co, Ni, Cu, Ag, or As and a is greater than 0.1 but less than 6, b has a value from 0 to 3, c has a value from 0.5 to 1.5, d has a value greater than 9 but less than 12, e has a value from 0.1 to 3, and f has a value determined by the valences and amounts of the other elements represented in the formula. The heteropolymolybdate mixtures preferably contain Cu, Cs, Rb, K, Ti, Ce, Mn, Fe, Bi, Cr, or As as component M.

Surprisingly, the catalysts prepared from the compositions in accordance with the invention have a life longer by a factor of from 5 to about 100 than prior art $H_5PMo_{10}V_2O_{40}$ or $Cu_{0.2}PMo_{10}VO_{35.2}$ heteropolyacid catalysts that are catalytically active and selective in oxydehydrogenation. Hence the new catalysts have a correspondingly higher productivity, expressed, for example, as kg of methacrylic acid per gram of catalytically effective heteropoly acids, and thus offer a decisive advantage over the prior art oxydehydrogenation catalysts.

The novel catalysts for the oxydehydrogenation of isobutyric acid or its esters are heteropolyacid and/or heteropolyacid salt mixtures comprising phosphomolybdic acid which are characterized in that the mixtures have an atomic ratio of Mo:V wherein Mo is greater than 9 but less than 12 and V is 0.1 or greater but less than 3, with an Mo:P atomic ratio wherein Mo is greater than 9 but less than 12 and P is from 0.5 to 1.5, preferably 1.

PRACTICE OF THE INVENTION

From the Mo-V-P atomic ratios indicated, which ratios are not limited to integers, it is apparent that the novel compositions, for example mixtures of various known heteropolyacids or their salt derivatives, such as of $H_3PMo_{12}O_{40}$ with $H_4PMo_{11}VO_{40}$ and/or with $H_5PMo_{10}V_2O_{40}$ and/or with $H_{2.4}Cu_{0.8}PMo_{11}VO_{40}$, or also of $H_4PMo_{11}VO_{40}$ with $H_5PMo_{10}V_2O_{40}$, may have different molar ratios and, as has been found, can be prepared by intensive mixing of such constituents. When used as catalysts in the oxydehydrogenation of isobutyric acid or its esters, mixtures of the heteropolyacids, such as a 1:1 molar mixture of $H_3PMo_{12}O_{40}$ and $H_4PMo_{11}VO_{40}$ which then has the overall composition $H_{3.5}PMo_{11.5}V_{0.5}H_{40}$, exhibit not only good activity but also significantly improved long term behavior.

However, it has further been found that the selectivity of the inventive mixed heteropolyacid catalysts is improved still more, and considerably so, if they contain metal ions. Heteropolyacid mixtures containing metal ions can be prepared, as indicated above, by admixing an appropriate metallic salt of a heteropolyacid, or by reacting at least a portion of the heteropolyacids present in the heteropolyacid mixture with further metal compounds to give their metallic salts. In this way, catalysts are obtained which not only have good activity and considerably improved long term properties, but also substantially better selectivity for methacrylic acid. A content of copper ion in the heteropoly acid mixtures has proved particularly advantageous. Such compositions are obtained, for example, by reacting heteropoly acid mixtures according to the invention with copper hydroxide, for example. With a composition of the invention such as $H_{3.1}Cu_{0.2}PMo_{11.5}V_{0.5}O_{40}$ used as a catalyst, selectivities for methacrylic acid of about 70 percent have been obtained, which represents an increase of more than 20 percent over that of a copper free catalyst. Substantial stabilization of this selectivity is secured by adding further metal ions, for example in a Cu/Cs metal ion combination.

Thus, the catalysts of the present invention are (A) a mixture of at least two members selected from the group consisting of
(i) $H_{3+x}PMo_{12-x}V_xO_{40}$, wherein x is 1, 2, or 3 and
(ii) metals salts thereof, the molar ratio of any member or combination of members to any other member in such a mixture being from 0.99:0.001 to 0.01:0.99, or consisting essentially of
(B) a mixture of at lest one member selected from the group consisting of (A)(i) and (A)(ii) and at least one member selected from the group consisting of
(iii) $H_3PMo_{12}O_{40}$ and
(iv) metal salts thereof,
the molar ratio of said member or members (A)(i) and (A)(ii) to said member or members (B)(iii) and (B)(iv) being from 0.9:01 to 0.1:0.9.

The composition of the inventive heteropoly acid mixture containing metal cations can be represented by the formula $H_aM_bP_cMo_dV_eO_f$ 

wherein M signifies one or more of the elements Li, Na, K, Rb, Cs, Be, Mg, Ca, Sr, Ba, Zn, Cd, Al, Ce, Ti, Zr, Sn, Sb, Pb, Bi, Cr, Mn, Fe, Co, Ni, Cu, Ag, or As and wherein a, b, c, d, e, and f have the values given earlier.

The preparation of the heteropolyacid metallic salts in admixture with free heteropolyacid is advantageously carried out by adding metal compounds such as metal hydroxides, metal carbonates, metal nitrates, or metal phosphates to mixtures of heteropolyacids, which latter can be made for example, as a paste with water to improve mixing. For better conversion to the heteropolyacid metallic salt, the mixture may be heated for a short time to about 100° C.

The preparation of the heteropolymolybdate mixture in the presence of a solid carrier is particularly preferred for preparation of the catalyst systems in accordance with the invention. Inert carrier materials comprising oxygen compounds of aluminum, titanium, and particularly silicon, or mixtures of various such oxygen compounds, or silicon carbide, are preferred.

The ratio of the catalytically active substance, that is of the heteropolymolybdate mixture of the general formula $H_aM_bP_cMo_dV_eO_f$ 

to the carrier may vary within certain limits. In general, the catalytically active substance will be from 5 to 80 percent, and preferably from 15 to 70 percent, of the total weight including the carrier. For use as a catalyst system, the product so obtained may be put into a proper size and shape, for example by granulation, pelletizing, or tableting. The size and shape of the catalysts to be used depend mainly on the reaction technique employed in the oxydehydrogation, for example reaction in a fixed bed reactor. Shaping may be followed by annealing of the catalyst system for from about 1 hour to about 24 hours, for example at temperatures ranging from 200° C. to 400° C.

The catalyst system in accordance with the present invention is distinguished by good activity and selectivity and at the same time by technically appropriate long term behavior in the oxidative dehydrogenation of isobutric acid or its esters, the latter being primarily the lower esters having from one to three carbon atoms in the alcohol group of the ester, and particularly isobutyric acid methyl ester. The conversion is effected at temperatures ranging from about 250° C. to about 400° C. and preferably between 300° C. and 380° C. The dwell time generally ranges from 0.1 to 5 seconds.

The oxydehydrogenation method in accordance with the present invention is a gas phase reaction with oxygen as the oxidizing agent, for example in the form of air. In addition to the isobutyric acid or ester and oxygen reagents, the gas mixture used in particular contains nitrogen and, optionally, also water in the form of steam. The molar ratio of the components of the gas mixture, in the order indicated, advantageously ranges from 1:(1–4):(4–20):(0–5) moles, the preferred molar ratio being 1:(1–2):(4–10):(0.5–2).

Experience has shown that the presence of water has a favorable effect on the reaction. The inventive mixed heteropolymolybdate catalysts can be used in the reactors commonly employed, for example using pressure. Suitable pressures range from 0.1 to 5 bar and are preferably from 0.5 to 2.5 bar. The catalysts should be adapted with respect to size and shape to the reaction technique to be used.

A better understanding of the present invention and of its many advantages will be had from the following Examples, given by way of illustration.

EXAMPLES

(A) Preparation of mixed catalysts

Example 1

$H_{3.5}PMo_{11.5}V_{0.5}O_{40}$ 0.063 mole of $H_4PMo_{11}VO_{40}$ is introduced into a reactor as a 10 weight percent aqueous solution and 0.063 mole of $H_3PMo_{12}O_{40}$ is then added.

The mixture is heated to reflux for 30 minutes at 100° C. The clear orange colored solution is mixed with 80.5 g of diatomaceous earth (kieselguhr) and 16.1 g of powdered silica gel and evaporated with stirring to leave a paste. The latter is oven dried for 1 hour at 110° C. and for 3 hours at 200° C. The catalyst is then calcined in a muffle furnace for 3 hours at 300° C. and crushed into pieces about 5 mm in size.

Example 2

$Cu_{0.2}H_{3.1}PMo_{11.5}V_{0.5}O_{40}$ 0.063 mole of $H_4PMo_{11}VO_{40}$ is introduced into a reactor as a 10 weight percent aqueous solution and 0.063 mole of $H_3PMo_{12}O_{40}$ and 0.0252 mole of CuO are added.

After brief boiling (for 5 minutes), 81.4 g of diatomaceous earth and 16.3 g of powdered silica gel are added. Further processing is carried out as in Example 1.

Example 3

$Cs_{0.2}H_{3.3}PMo_{11.5}V_{0.5}O_{40}$ 0.063 mole of $H_4PMo_{11}VO_{40}$ is used as a 10 weight percent aqueous solution and 0.063 mole of $H_3PMo_{12}O_{40}$ and 0.0126 mole of $Cs_2CO_3$ are added.

The mixture is mixed with 81.4 g of diatomaceous earth and 16.3 g of powdered silica gel, evaporated with stirring to leave a paste, and further processed as described in Example 1.

Preparation of comparative catalysts

Comparative Example 1

$H_4PMo_{11}VO_{40}$

The heteropolyacid was prepared as described in U.S. Pat. No. 4,146,574. The preparation of a 70 percent catalyst was carried out as described in Example 1.

Comparative Example 2

$Cu_{0.2}H_{3.6}PMo_{11}VO_{40}$

The preparation of the 70 percent $Cu_{0.2}H_{3.6}PMo_{11}VO_{40}$ catalyst was carried out as described in Example 2.

Comparative Example 3

$Cs_{0.1}H_{3.9}PMo_{11}VO_{40}$ 0.063 mole of $H_4PMo_{11}V_1O_{40}$ is used as a 10 weight percent solution and 0.0032 mole of $Cs_2CO_3$ is added. The further preparation of a 70 percent catalyst is carried out as described in Example 3.

Example 4

$Cu_{0.05}Cs_{0.1}H_{3.3}PMo_{11.5}V_{0.5}O_{40}$ 0.063 mole of $Cu_{0.1}H_{3.8}PMo_{11}VO_{40}$ is used as a 10 weight percent aqueous solution and 0.063 mole of $H_3PMo_{12}O_{40}$ and 0.0063 mole of $Cs_2CO_3$ are added.

The mixture is heated in a 3-liter beaker for 30 minutes, mixed with 81.4 g of diatomaceous earth and 16.3 g of powdered silica gel, and processed further as described in the other Examples.

(B) Oxydehydrogenation of isobutyric acid

Examples 1 to 4 and comparative Examples 1 to 3

General testing procedure

A vaporous mixture of isobutyric acid and oxygen (as air) in a molar ratio of 1:1:5 is reacted over the 70 percent catalysts (see following Table I) in a circulating reactor known in the art (cf. published German Patent Application DOS 30 19 731) at 320° C. and with a dwell time of 0.6 second. The catalyst loading is 2.5 kg of isobutyric acid per kg of catalytic mass per hour. The reaction gas is then analyzed by gas chromatography.

TABLE I

| CATALYST as prepared in | Catalytically effective substance | CONVERSION (%)* | | | SELECTIVITY (%)* | | |
|---|---|---|---|---|---|---|---|
| | | $C_1$ | $C_{250}$ | $C_{500}$ | $S_1$ | $S_{250}$ | $S_{500}$ |
| Example 1 | $H_{3.5}PMo_{11.5}V_{0.5}O_{40}$ | 71 | 73 | 71 | 50 | 53 | 55 |
| Comparative example 1 | $H_4PMo_{11}V_1O_{40}$ | 75 | 71 | 64 | 60 | 60 | 60 |
| Example 2 | $Cu_{0.2}H_{3.1}PMo_{11.5}V_{0.5}O_{40}$ | 64 | 57 | 47 | 72 | 66 | 58 |
| Comparative example 2 | $Cu_{0.2}H_{3.6}PMo_{11}V_1O_{40}$ | 50 | 20 | — | 72 | 61 | — |
| Example 3 | $Cs_{0.2}H_{3.3}PMo_{11.5}V_{0.5}O_{40}$ | 65 | 58 | 52 | 55 | 62 | 62 |
| Comparative example 3 | $Cs_{0.1}H_{3.9}PMo_{11}V_1O_{40}$ | 69 | 48 | 39 | 63 | 66 | 62 |
| Example 4 No Comparative example | $Cu_{0.05}Cs_{0.1}H_{3.3}PMo_{11.5}V_{0.5}O_{40}$ | 64 | 61 | 53 | 70 | 71 | 68 |

*After the number of hours indicated by the subscripts.

Example 5

$Cr_{0.2}H_{3.3}PMo_{10.5}V_{1.5}O_{40}$

A 10 percent by weight solution of 0.063 mole of $H_4PMo_{11}VO_{40}$ and a 10 percent solution of 0.063 mole of $H_5PMo_{10}V_2O_{40}$ are combined at room temperature and then further mixed with a 10 percent solution of 0.025 mole of $CrO_3$.

The resulting solution is combined with 80.5 g of kieselguhr and 16.1 g of powdered silica gel and further worked up as in Example 1.

Example 6

$Fe_{0.2}Bi_{0.2}H_{2.3}PMo_{11.5}V_{0.5}O_{40}$ 0.063 mole of $H_4PMo_{11}VO_{40}$ is prepared as a 10 percent aqueous solution and 0.063 mole of $H_3PMo_{12}O_{40}$ is added. 0.025 mole of iron(III)nitrate · $H_2O$ and 0.025 mole of bismuth(III)nitrate · $5H_2O$ are dissolved in about 15 ml of $HNO_3$ and are added to the solution of $H_{3.5}PMo_{11.5}V_{0.5}O_{40}$.

The solution is combined with 80.5 g of kieselguhr and 16.1 g of powdered silica gel and further worked up as in Example 1.

Examples 7–10

The preparation of these catalysts follows the procedures given in Example 5. For dosing with metal according to the formulas given in following Table II, Ce was added as $Ce(NO_3)_4$, Mn as $Mn(CO_3)_2$, Ti as $Ti(O\text{-}i\text{-}propyl)_4$, Cu as CuO, and Cs as $Cs_2CO_3$.

Example 11

$Cu_{0.2}H_{2.8}PMo_{11.8}V_{0.2}O_{40}$ 0.1 mole of $H_3PMo_{12}O_{40}$ is dissolved together with 0.025 mole of CuO in 500 ml of $H_2O$ with stirring at 100° C. and subsequently combined with 0.025 mole of $H_4PMo_{11}VO_{40}$ (20 percent solution by weight).

The clear solution is combined with 82.2 g of kieselguhr and 16.4 g of powdered silica gel and further worked up as in Example 1.

Example 12

$Cu_{0.2}As_{0.1}H_{2.3}PMo_{11.8}V_{0.2}O_{40}$ 0.1 mole of $H_3PMo_{12}O_{40}$ is dissolved together with 0.0063 mole of $As_2O_5$ and 0.025 mole of CuO in 500 ml of $H_2O$ with stirring at 100° C. and subsequently combined with 0.025 mole of $H_4PMo_{11}VO_{40}$ (20 percent solution by weight). The clear solution is combined with 82.2 g of kieselguhr and 16.4 g of powdered silica gel and further worked up as in Example 1.

Example 13

$H_{4.6}PMo_{10.4}V_{1.6}O_{40}$ 1.3 mole of $MoO_3$ are heated for 24 hours at 100° C. together with 0.1 mole of $V_2O_5$ and 0.125 mole of $H_3P_4$ (85.9 percent) in 2000 g of distilled water.

The solution is worked up as in Example 1.

Example 14

$Rb_{0.2}H_{3.3}PMo_{11.5}V_{0.5}O_{40}$ 0.063 mole of $H_3PMo_{12}O_{40}$ and 0.025 mole of $RbNO_3$ are added to a 10 percent aqueous solution of 0.063 mole of $H_4PMo_{11}VO_{40}$.

The mixture is combined with 80.5 g of diatomaceous earth and 16.1 g of powdered silica gel and worked up as in Example 1.

Example 15

$K_{0.1}H_{4.4}PMo_{10.5}V_{1.5}O_{40}$

The catalyst is prepared as in Example 5. K is added as $KNO_3$ in an amount required by the formula.

Preparation of the Comparative Catalysts

The catalysts for comparative Examples 5–9, 11, and 13 are prepared by a procedure analogous to that used in the Examples to which they pertain by combination of the relevant metal compound with $H_5PMo_{10}V_2O_{40}$ or $H_4PMo_{11}VO_{40}$.

B. Oxydehydrogenation of Isobutyric Acid

The catalysts of Examples 5–15 and comparative Examples 5–9, 11 and 13 were used for the oxydehydration of isobutyric acid using the following general test procedure:

A vaporous mixture of isobutyric acid, oxygen (from air), and nitrogen in a mole ratio of 1:1.5:7.71 is reacted by passing it over the 70 percent catalyst (cf. Table II) in a circulating reactor at 340° C. with a dwell time of 1 second. The loading of the catalyst is 1.25 kg of isobutyric acid/kg of catalytic mass/hr. The reaction gas is subsequently analyzed by gas chromatography.

Conversion and selectivity as a function of time are reported in Table II.

TABLE II

| Catalyst as prepared in | Catalytically effective substance | Conversion* (%) | | | Selectivity* (%) | | |
|---|---|---|---|---|---|---|---|
| Example 5 | $Cr_{0.2}H_{3.3}PMo_{10.5}V_{1.5}O_{40}$ | $C_0$ 74.3 | $C_{4.8}$ 71.5 | $C_{72}$ 69.2 | $S_0$ 67.5 | $S_{48}$ 70.8 | $S_{72}$ 71.2 |
| Comparative Example 5 | $Cr_{0.2}H_{3.8}PMo_{10}V_2O_{40}$ | $C_0$ 61.4 | $C_{51}$ 58.5 | $C_{74}$ 53.9 | $S_0$ 66.0 | $S_{51}$ 67.0 | $S_{74}$ 64.4 |
| Example 6 | $Fe_{0.2}Bi_{0.2}H_{2.3}PMo_{11.5}V_{0.5}O_{40}$ | $C_0$ 82.5 | $C_{60}$ 83.8 | $C_{100}$ 82.8 | $S_0$ 61.8 | $S_{60}$ 61.1 | $S_{100}$ 60.5 |
| Comparative Example 6 | $Fe_{0.2}Bi_{0.2}H_{2.8}PMo_{11}VO_{40}$ | $C_0$ 82.5 | $C_{40}$ 79.6 | $C_{86}$ 77.4 | $S_0$ 67.0 | $S_{40}$ 70.5 | $S_{86}$ 69.0 |
| Example 7 | $Ce_{0.2}H_{3.7}PMo_{10.5}V_{1.5}O_{40}$ | $C_0$ 86.5 | $C_{55}$ 86.8 | $C_{128}$ 86.7 | $S_0$ 71.0 | $S_{55}$ 70.9 | $S_{128}$ 71.7 |
| Comparative Example 7 | $Ce_{0.2}H_{4.2}PMo_{10}V_2O_{40}$ | $C_{30}$ 74.1 | $C_{80}$ 72.8 | $C_{124}$ 70.9 | $S_{30}$ 72.5 | $S_{79}$ 70.6 | $S_{124}$ 76.0 |
| Example 8 | $Mn_{0.2}H_{4.1}PMo_{10.5}V_{1.5}O_{40}$ | $C_0$ 82.8 | $C_{63}$ 80.5 | $C_{71}$ 79.7 | $S_0$ 66.4 | $S_{63}$ 68.9 | $S_{71}$ 71.9 |
| Comparative Example 8 | $Mn_{0.2}H_{4.6}PMo_{10}V_2O_{40}$ | $C_{18}$ 71.0 | $C_{72}$ 62.0 | $C_{94}$ 59.9 | $S_{18}$ 75.7 | $S_{71}$ 70.7 | $S_{94}$ 64.0 |
| Example 9 | $Ti_{0.2}H_{3.7}PMo_{10.5}V_{1.5}O_{40}$ | $C_0$ 77.4 | $C_{47}$ 79.2 | $C_{73}$ 78.4 | $S_0$ 72.5 | $S_{47}$ 74.4 | $S_{73}$ 74.5 |
| Comparative Example 9 | $Ti_{0.2}H_{4.2}PMo_{10}V_2O_{40}$ | $C_0$ 70.9 | $C_{48}$ 68.3 | $C_{73}$ 66.6 | $S_0$ 74.1 | $S_{48}$ 75.4 | $S_{73}$ 72.8 |
| Example 10 | $Cu_{0.1}Cs_{0.1}H_{4.2}PMo_{10.5}V_{1.5}O_{40}$ | $C_0$ 84.1 | $C_{46}$ 83.3 | $C_{73}$ 83.8 | $S_0$ 75.3 | $S_{46}$ 76.2 | $S_{73}$ 76.0 |
| No Comparative Example | | | | | | | |
| Example 11 | $Cu_{0.2}H_{2.8}PMo_{11.8}V_{0.2}O_{40}$ | $C_0$ 90.6 | $C_{56}$ 89.3 | $C_{75}$ 88.8 | $S_0$ 55.6 | $S_{56}$ 56.3 | $S_{75}$ 56.8 |
| Comparative Example 11 | $Cu_{0.2}H_{3.6}PMo_{11}VO_{40}$ | $C_0$ 81.5 | $C_{48}$ 79.8 | $C_{95}$ 76.5 | $S_0$ 72.9 | $S_{48}$ 77.3 | $S_{95}$ 77.7 |
| Example 12 | $Cu_{0.2}As_{0.1}H_{2.3}PMo_{11.8}V_{0.2}O_{40}$ | $C_0$ 85.5 | $C_{50}$ 84.5 | $C_{72}$ 84.8 | $S_0$ 62.8 | $S_{50}$ 65.1 | $S_{72}$ 63.7 |
| No Comparative Example | | | | | | | |
| Example 13 | $H_{4.6}PMo_{10}V_{1.6}O_{40}$ | $C_{42}$ 85.5 | $C_{66}$ 85.9 | $C_{90}$ 86.3 | $S_{42}$ 71.3 | $S_{65}$ 72.9 | $S_{90}$ 73.1 |

TABLE II-continued

| Catalyst as prepared in | Catalytically effective substance | Conversion* (%) | | | Selectivity* (%) | | |
|---|---|---|---|---|---|---|---|
| Comparative Example 13 | $H_5PMo_{10}V_2O_{40}$ | $C_0$ 80.4 | $C_{26}$ 80.1 | $C_{54}$ 80.4 | $S_0$ 68.0 | $S_{26}$ 68.4 | $S_{54}$ 68.4 |
| Example 14 ** | $Rb_{0.2}H_{3.3}PMo_{11.5}V_{0.5}O_{40}$ | $C_{21}$ 84.1 | $C_{43}$ 84.0 | $C_{117}$ 84.0 | $S_{21}$ 63.5 | $S_{43}$ 63.7 | $S_{117}$ 64.0 |
| Example 15 ** | $K_{0.1}H_{4.4}PMo_{10.5}V_{1.5}O_4$ | $C_0$ 81.0 | $C_{50}$ 80.8 | $C_{80}$ 80.8 | $S_0$ 69.5 | $S_{50}$ 70.5 | $S_{80}$ 70.8 |

*After the number of hours indicated by the subscripts.
**No Comparative Example

What is claimed is:

1. A composite heteropolymolybdate catalyst, adaptable to the oxydehydrogenation of isobutyric acid or a lower ester thereof to methacrylic acid or a lower ester thereof, respectively, said composite catalyst being a mixture having the formula, for the composite of $$H_aM_bP_cMo_dV_eO_f,$$

wherein M is at least one member selected from the group consisting of Li, Na, K, Rb, Cs, Be, Mg, Ca, Sr, Ba, Zn, Cd, Al, Ce, Ti, Zr, Sn, Sb, Pb, Bi, Cr, Mn, Fe, Co, Ni, Cu, Ag, and As, a is greater than 0.1 but less than 6, b is 0 to 3, c is 0.5 to 1.5, d is greater than 9 but less than 12, e is 0.1 to 3, and f has a value determined by the valences and amounts of the elements other than oxygen, and consisting essentially of (A) a mixture of at least two members selected from the group consisting of
  (i) $H_{3+x}PMo_{12-x}V_xO_{40}$, wherein x is 1, 2, or 3 and
  (ii) metals salts thereof,
  the molar ratio of any member or combination of members to any other member in such a mixture being from 0.99:0.001 to 0.001:0.99, or consisting essentially of
(B) a mixture of at least one member selected from the group consisting of said mixture (A)(i) and (A)(ii) and at least one member selected from the group consisting of
  (iii) $H_3PMo_{12}O_{40}$ and
  (iv) metal salts thereof,
  the molar ratio of said member (A)(i) and (A)(ii) to said member or members (B)(iii) and (B)(iv) being from 0.9:01 to 0.1:0.9.

2. A catalyst as in claim 1 wherein b is 0.05 to 2.5.

3. A catalyst as in claim 1, wherein M is Cu, Cs, Rb, K, Ti, Ce, Mn, Fe, Bi, Cr, or As.

4. A catalyst as in claim 1 wherein M is at least one member selected from the group consisting of copper and cesium.

5. A catalyst as in claim 1 present on an inert carrier.

6. A method for the oxidative dehydrogenation of isobutyric acid or a lower ester thereof to methacrylic acid or a lower ester thereof, which method comprises contacting a gaseous mixture of said isobutyric acid or a lower ester thereof and oxygen in the presence of a catalyst as in claim 1.

7. A method as in claim 6 wherein b is 0.05 to 2.5.

8. A method as in claim 6 wherein M is at least one member selected from the group consisting of Cu, Cs, Rb, K, Ti, Ce, Mn, Fe, Bi, Cr, and As.

9. A method as in claim 6 wherein M is at least one member selected from the group consisting of copper and cesium.

* * * * *